United States Patent [19]

Amundson

[11] Patent Number: 4,722,342
[45] Date of Patent: Feb. 2, 1988

[54] CARDIAC PACER FOR PACING A HUMAN HEART AND PACING METHOD

[75] Inventor: David Amundson, Bromma, Sweden

[73] Assignee: Siemens Aktiengesellschaft, Berlin and Munich, Fed. Rep. of Germany

[21] Appl. No.: 874,588

[22] Filed: Jun. 16, 1986

[51] Int. Cl.4 .............................................. A61N 1/36
[52] U.S. Cl. ............................ 128/419 PG; 128/661
[58] Field of Search ........................................ 128/661

[56] References Cited

U.S. PATENT DOCUMENTS

| | | | |
|---|---|---|---|
| 3,561,430 | 2/1971 | Filler | 128/661 |
| 4,140,132 | 2/1979 | Dahl | 128/419 PG |
| 4,270,547 | 6/1981 | Steffen et al. | 128/671 |
| 4,399,820 | 8/1983 | Wirtzfeld et al. | 128/419 PG |
| 4,428,378 | 1/1984 | Anderson et al. | 128/419 PG |
| 4,473,078 | 9/1984 | Angel | 128/419 PG |
| 4,513,743 | 4/1985 | van Arragon et al. | 128/419 PG |
| 4,527,568 | 7/1985 | Rickards | 128/419 PG |
| 4,543,954 | 10/1985 | Cook et al. | 128/419 PG |
| 4,579,119 | 4/1986 | Callaghan | 128/419 PG |
| 4,596,251 | 6/1986 | Plicchi et al. | 128/419 PG |

FOREIGN PATENT DOCUMENTS 2403775  9/1977  France ..................... 128/419 PG Primary Examiner—William E. Kamm
Assistant Examiner—Timothy Keegan
Attorney, Agent, or Firm—Hill, Van Santen, Steadman & Simpson

[57] ABSTRACT

A cardiac pacer, which generates pacing pulses at a predetermined basic pacing rate, includes a multiplicity of body activity sensors for sensing body activity dependent on different physiological variables and monitors for generating a corresponding body activity output signal dependent thereon. The predetermined basic pacing rate is then varied dependent on the body activity output signals.

16 Claims, 3 Drawing Figures

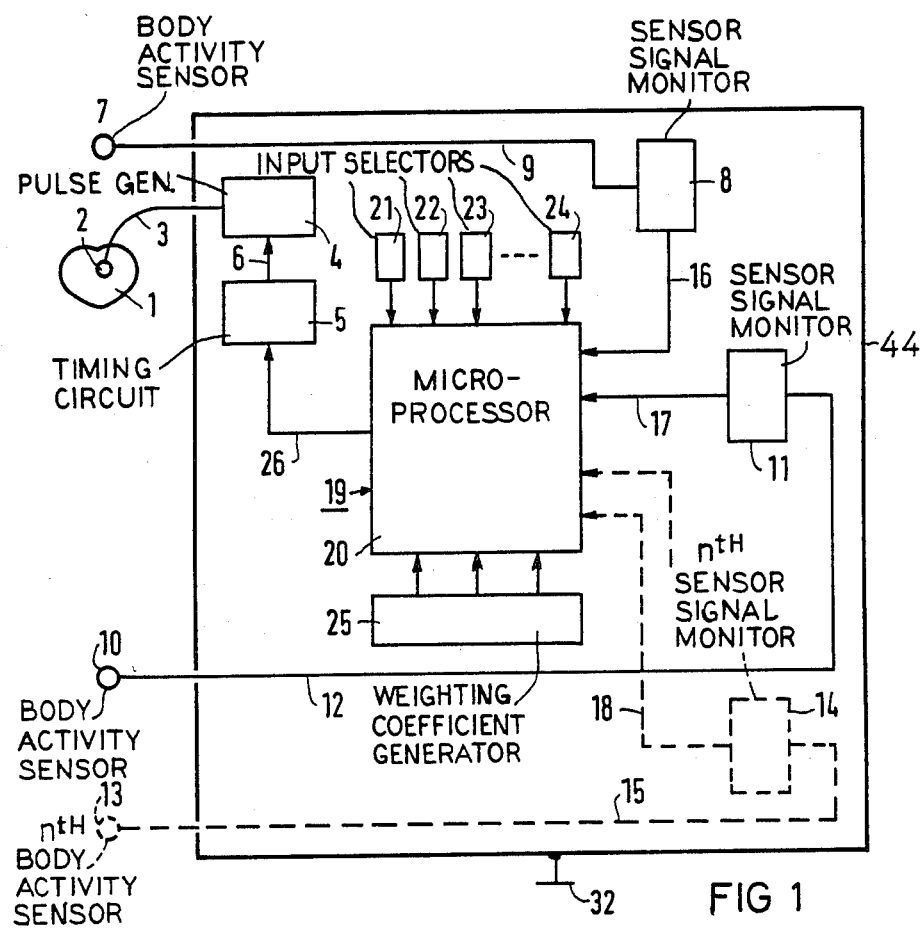
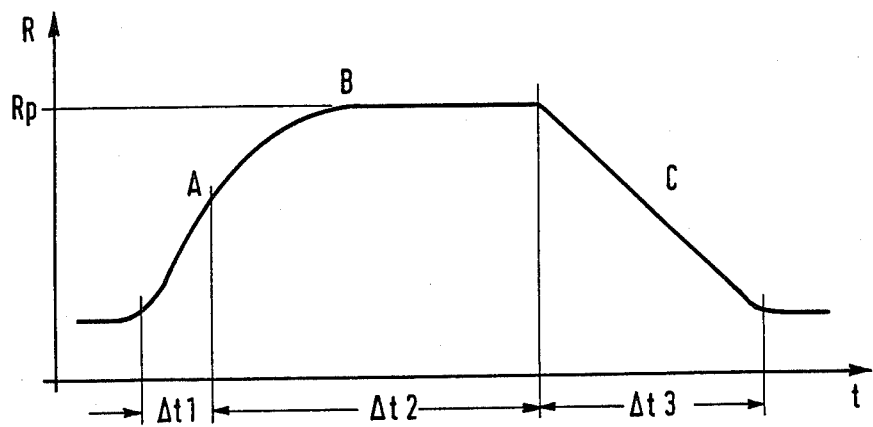

CARDIAC PACER FOR PACING A HUMAN HEART AND PACING METHOD

BACKGROUND OF THE INVENTION

1. Field of the Invention

The invention relates to a cardiac pacer for pacing a heart, in particular a human heart, wherein the pacing rate is controlled by a signal that is dependent upon physical activity or a measured physiological change in the body of a patient.

2. Related Applications

The subject matter of the present application is related to the subject matter of the following co-pending applications filed simultaneously herewith: "A Cardiac Pacer For Pacing A Heart," Elmqvist, Lekholm, Hedberg and Amundson, Ser. No. 874,597; "A Cardiac Pacer For Pacing A Heart," Lekholm and Amundson, Ser. No. 874,596; "A Cardiac Pacer For Pacing A Heart," Lekholm and Amundson, Ser. No. 874,585.

3. Description of the Prior Art

Conventional cardiac pacers of the respiration rate-responsive type are, for example, described in U.S. Pat. No. 3,593,718 and in European Patent Application No. 0,089,014. An accerlerameter rate-responsive cardiac pacer is, for example, depicted in U.S. Pat. No. 4,428,378.

One of the main difficulties with these rate-responsive cardiac pacers is that it is difficult to exactly determine different exercise stages, such as the start, duration and termination of an exercise for a patient wearing such a cardiac pacer.

SUMMARY OF THE INVENTION

1. Objects

It is an object of this invention to provide for an improved cardiac pacer comprising a sensor arrangement which is adequate for correctly determining different exercise stages, such as the start, duration and termination of an exercise.

2. Summary

According to this invention an improved cardiac pacer is provided which comprises
  (a) means for generating pacing pulses at a predetermined basic pacing rate;
  (b) means for transmitting the pacing pulses to the heart for pacing;
  (c) a multiplicity of body activity sensor means for sensing body activity dependent on different physiological variables and for respectively generating a corresponding body activity output signal dependent thereon; and
  (d) means for varying the predetermined basic pacing rate dependent on said body activity output signals.

According to this invention two or more different sensors for differnet physiological variables yield better quality information at different points in the exercise period. For example, a respiration (or e.g. temperature) sensor is not a very good sensor for determining the start of exercise, yet it is a very good sensor for detemining whether or not the exercise has continued. Conversely, an accelerometer is very suitable for determining the start of exercise but is less reliable in determining the duration of the exercise or the termination of the exercise.

The foregoing and other objects, features and advantages of the invention will be apparent from the following more particular description of a preferred embodiment of the invention, as illustrated in the accompanying drawings.

BRIEF DESCRIPTION OF THE DRAWINGS

FIG. 1 shows an embodiment of a cardiac pacer comprising the invention in a schematic block diagram;

FIG. 2 shows a diagram illustrating a pacing rate R as a function of time t during an exercise period.

DESCRIPTION OF THE PREFERRED EMBODIMENT

Figure 3:
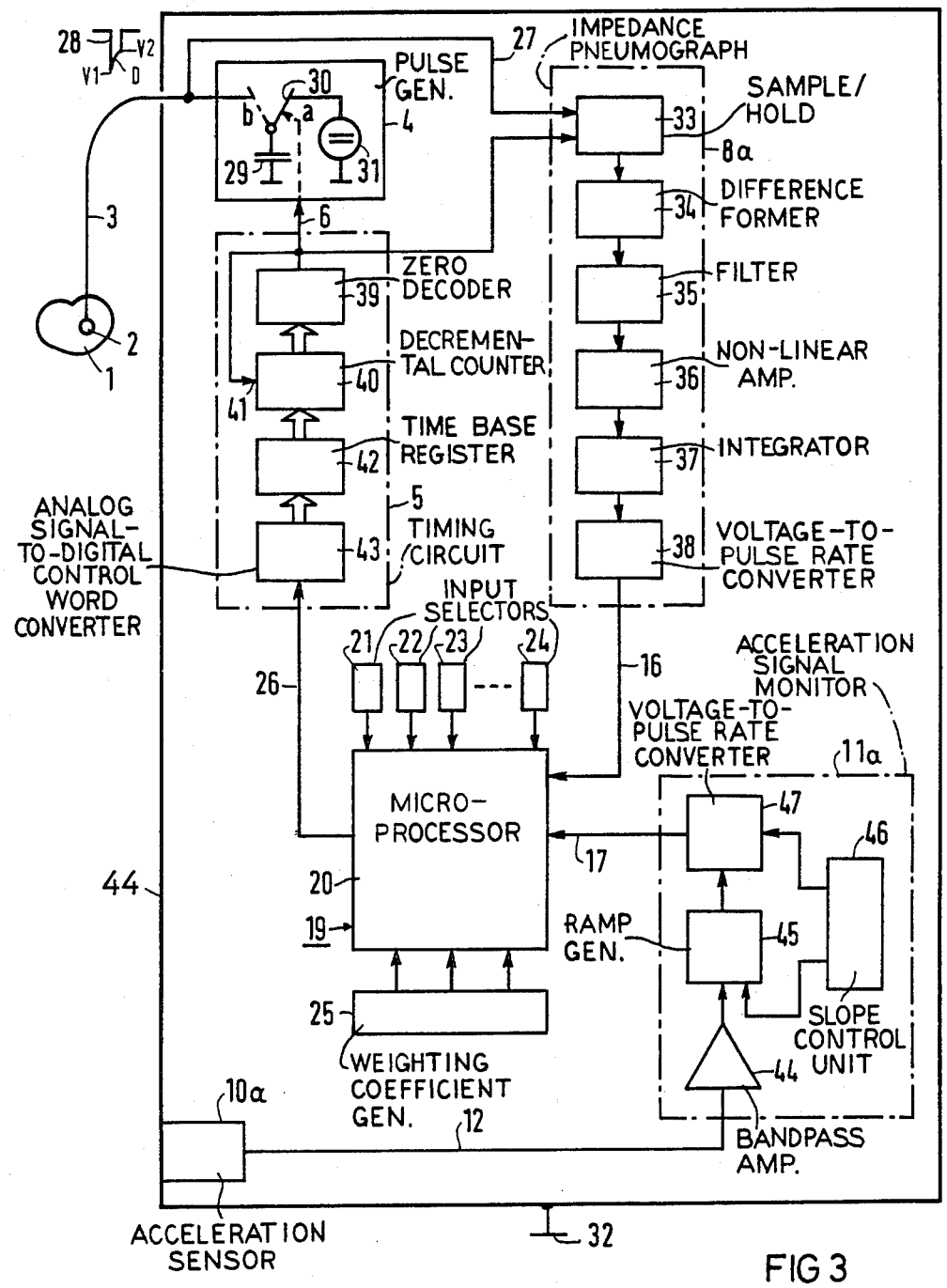
FIG. 3 shows an embodiment of a cardiac pacer according to FIG. 1 including two sensors and following the diagram according to FIG. 2 in more detail.

In FIG. 1 a human heart which has to be paced is generally designated with 1. A pacing electrode 2 is inserted in the human heart 1 in a manner and position that the heart can most efficiently be paced. The pacing electrode 2 is connected through a pacing lead 3 with a pacing pulse generator 4. A timing circuit 5 controls the pacing rate of the pacing pulse generator 4 through line 6.

A first snesor 7 for physical activity dependent on a first physiological variable is connected with a first body activity sensor monitor 8 through line 9. A second sensor 10 for physical activity dependent on a second physiological variable is connected with a second body activity sensor monitor 11 through line 12. Both sensors 7 and 10 are also preferably implanted in the patient's body. The sensor arrangement, if desired, may be extended by more body activity sensors and associated body activity sensor circuitries as indicated in FIG. 1 in broken lines by an n-th body activity sensor 13 for an n-th physiological variable which is connected with an associated n-th body activity sensor monitor 14 through line 15.

The different body activity sensors 7, 10 and 13 are designed to sense body activity in different exercise stages, e.g. start, duration and termination of exercise, dependent on different physiological variables, e.g. acceleration, respiration, temperature, pH, $pO_2$ etc.. The associated body activity sensor monitors 8, 11 and 14 generate corresponding body activity output signals which are supplied through respective lines 16, 17 and 18 to selector circuitry generally referenced at 19.

The selector circuitry 19, which may include, e.g., a microprocessor 20 or any kind of appropriate selective logic circuitry in combination with input selectors 21 to 24 and, for example, a weighting coefficient generator 25, is designed for selecting single activity output signals and/or combinations thereof to determine different exercise stages dependent on different physiological variables. For example the input selector 21 may serve for successively selecting single activity output signals and/or combinations thereof in predetermined time steps after the start of an exercise cycle. Accordingly the input selectors 22, 23 and 24 may, for example, be designed for selecting single activity output signals and/or combinations thereof dependent on predetermined pacing rates, dependent on activity output signals which fluctuate least and/or dependent on whether or not a single activity output signal and/or combinations thereof fall(s) below a threshold.

The output of the selector circuitry 19 is connected with the timing circuit 5 through line 26. Under the circumstances the timing circuit 5 is designed for varying the predetermined basic pacing rate dependent on the selected single or the combination of selected single output signals of the body activity sensor monitors 8, 11 and 14.

In FIG. 1 the pacing pulse generator 4, the timing circuit 5, the body activity sensor monitors 8, 11 and 14 and the selector circuitry 19 are all encapsulated in an implantable conductive (metallic) housing 27 which is the housing to the cardiac pacer according to this invention.

FIGS. 2 and 3 illustrate an embodiment of the invention according to FIG. 1, wherein a acceleration sensor 10a and an associated acceleration sensor monitor 11a are utilized to determine the start of exercise (time period A in FIG. 2) and a respiration sensor (pacing electrode 2) and an associated respiration sensor monitor 8a are used to determine the duration and termination of exercise (time periods B and C in FIG. 2) according to predetermined time steps $\Delta$ t1, $\Delta$ t2, $\Delta$ t3 after start of exercise. The time steps may be predetermined by means of time steps input selector 21 of the selector circuitry 19. They may, for example, be selected in the ranges of $\Delta$ t1 = 10–60s, $\Delta$ t2 = 30s–20 min, $\Delta$ t3 = 30s 3 min. The peak value of the pacing rate is indicated in FIG. 2 with Rp.

In FIG. 3 the respiration sensor circuitry 8a is an impedance pneumograph which is connected with the pacing pulse generator 4 through line 27 for processing the pacing pulses 28 such that a respiratory signal is obtained from the pacing pulses 28 when evaluating the amplitude decays D of pacing pulses 28. The amplitude decay D changes according to alternating body impedance during respiration.

The pacing pulse generator 4 comprises an output capacitor 29 which is switchable by means of switch 30 between battery 31 (switch position a) and pacing lead 3 (switch position b). In switch position a the output capacitor 29 is charged by the battery 31 to a voltage V1. In switch position b the output capacitor 29 is discharged through pacing lead 3 as pacing pulse 20. The amount of discharge depends on the impedance variations of the patient's thorax during respiration. According to FIG. 3 the pacing pulse 28 discharges from V1 to V2 (amplitude decay D). The conductive housing 44 serves as both the passive electrode for pacing and the electrode for impedance measurement (indicated by reference numeral 32). The impedance measurement may also be done by a division of voltage and current.

The impedance pneumograph 8a includes sample and hold circuitry 33, a difference former 34, a filter 35, non-linear (e.g. squaring) amplification circuitry 36 and an integrator 37 and a voltage to pulse rate converter 38. The sample and hold circuitry 33 samples and holds the voltages V1, V2 of output capacitor 29. The difference former 34 supplies the difference V1 - V2 through filter 35 to the non-linear amplification circuitry 36. The non-linear amplification circuitry 36 amplifies the output signal of filter 35 such that signal portions having higher amplitudes are more amplified than signal portions having lower amplitudes. Under the circumstances signal portions of interest including the respiration signal are enhanced with respect to low amplitude noise for further processing. Non-linear amplification circuitries of this kind are well known in the art and need not be described in more detail. The output signal of the non-linear amplification circuitry 36 is integrated in integrator 37 over a certain time period, e.g. in the range of 5 to 30 s. By integrating high-frequency noise is significantly reduced. The voltage to pulse rate converter 38 converts the integrated signal into a pulse rate according to the breathing rate.

The timing circuit 5 comprises a zero decoder 39, a decremental counter 40 having a reset input 41, a time base register 42 and an analog signal to digital control word converter 43. The converter 43 converts the output signal of the selector circuitry 19 into a digital control word. This digital control word is supplied to the time base register 42. It controls the time base regsister 42 such that a basic pacing rate, e.g. 60 beats/min., is varied dependent on the acceleration rate in time period A and on the respiration rate in time periods B and C of the exercise cycle according to FIG. 2. When the acceleration or breathing rate increases the time base register 42 increases the counting speed of the decremental counter 40 so that it reaches zero faster than at the basic rate. Under these conditions the zero decoder 39 generates switching signals at higher rates, so that the output capacitor 29 of the pacing pulse generator 4 charges and discharges at higher rates. As a result the pacing rate increases depending on increasing acceleration or breathing rate. It also decreases when acceleration and breathing rate are decreasing.

In FIG. 3 the acceleration sensor 10a includes e.g. a piezoelectric force sensor coupled to the housing 44 of the pacer for converting vibrational energy at the pacer site into a sensed acceleration signal. The sensed aceleration signal is applied to the acceleration sensor monitor 11a, which, for example, according to U.S. Pat. No. 4,428,378 comprises a bandpass amplifier 44, a ramp generator 45, a slope control unit 46 and a voltage to pulse rate converter 47.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto.

What is claimed is:

1. A cardiac pacer for pacing a human heart in a patient comprising:
   (a) means for generating pacing pulses at a predetermined basic pacing rate;
   (b) means for transmitting the pacing pulses to the heart for pacing thereof;
   (c) a plurality of body activity sensor means for respectively sensing body activity dependent on different physiological variables and for respectively generating a corresponding body activity output signal dependent thereon;
   (d) means for selecting single activity output signals and/or combinations thereof to determine different exercise stages dependent on different physiological variables; and
   (e) means conected to said means for generating pacing pulses and to said means for selecting for varying the predetermined basic pacing rate dependent on the selected body activity output signal or combination of signals.

2. A cardiac pacer as claimed in claim 1, wherein said means for selecting includes means for weighting single activity output signals and/or combinations thereof by different coefficients.

3. A cardiac pacer as claimed in claim 1, wherein said means for selecting includes means for successively selecting single activity output signals and/or combination thereof in predetermined time steps after the start of an exercise cycle.

4. A cardiac pacer as claimed in claim 1, wherein said means for selecting includes means for selecting single activity output signals and/or combinations thereof dependent on predetermined pacing rate values.

5. A cardiac pacer as claimed in claim 1, wherein said means for selecting includes means for selecting single activity output signals and/or combinations thereof dependent on activity output signals which fluctuate least.

6. A cardiac pacer as claimed in claim 1, wherein said means for selecting includes means for selecting single activity output signals and/or combinations thereof dependent on whether a single activity output signal and/or combinations thereof fall below a threshold.

7. A cardiac pacer as claimed in claim 6, wherein said means for selecting includes means for programming said threshold.

8. A cardiac pacer as claimed in claim 1, wherein one of said body activity sensor means includes means for obtaining a signal which is a physiological indication of the start of exercise by said patient.

9. A cardiac pacer as claimed in claim 1, wherein one of said body activity sensor means includes means for obtaining a signal which is a physiological indication of the duration of exercise by said patient.

10. A cardiac pacer as claimed in claim 1, wherein one of said body activity sensor means includes means for obtaining a signal which is a physiological indication of the duration and termination of exercise by said patient.

11. A cardiac pacer as claimed in claim 8, wherein said body activity sensor means is an acceleration sensor.

12. A cardiac pacer as claimed in claim 9, wherein said body activity sensor means is a respiration sensor.

13. An implantable cardiac pacer for pacing a heart in a patient comprising:
   means for generating pacing pulses at a predetermined pacing rate;
   means for transmitting the pacing pulses to the heart for pacing thereof;
   a first sensor for sensing a first physiological variable of said patient for generating a signal indicating a start of exercise by said patient;
   a second sensor for sensing a second physiological variable of said patient indicating the duration of said exercise by said patient;
   means in said implantable pacer for generating a signal corresponding to said second physiological variable sensed by said second sensor; and
   means connected to said first and second means for generating signals and to said means for generating pacing pulses for selecting one or a combination of said respective signals from said first and second means for generating signals to determine different exercise stages of said patient and means for varying said determined basic pacing rate in dependence upon said signals.

14. A pacer as claimed in claim 13, wherein said first sensor is an acceleration sensor.

15. A pacer as claimed in claim 13, wherein said second sensor is a respiration sensor.

16. A method for pacing a heart in a patient using a single implantable unit comprising the steps of:
   generating pacing pulses in said unit at a predetermined basic pacing rate:
   transmitting said pacing pulses to the heart for pacing thereof;
   sensing a plurality of physiological variables of said patient indicating body activity of said patient including sensing at least a physiological variable indicating a start of exercise by said patient using an acceleration sensor and a physiological variable indicating the duration of said exercise using a respiration sensor;
   generating respective signals in said unit corresponding to each of the sensed physiological variables;
   determining different exercise stages of said patient based on one or a combination of said signals; and
   varying said predetermined basic pacing rate in said unit dependence on the determined exercise stage.

* * * * *